US012759986B2

(12) United States Patent
Daintree et al.

(10) Patent No.: US 12,759,986 B2
(45) **Date of Patent: *Oct. 13, 2026**

(54) CRYSTAL FORMS OF TETRAHYDRO-N, N-DIMETHYL-2,2-DIPHENYL-3-FURANMETHANAMINE, PROCESSES OF MAKING SUCH FORMS, AND THEIR PHARMACEUTICAL COMPOSITIONS

(71) Applicant: ANAVEX LIFE SCIENCES CORP., New York, NY (US)

(72) Inventors: Linda Sharon Daintree, Leeds (GB); Daniel Mark Ledger, Bradford (GB); Lucy Anne Leonard, Bradford (GB); Peter York, Bradford (GB)

(73) Assignee: ANAVEX LIFE SCIENCES CORP., New York, NY (US)

( * ) Notice: Subject to any disclaimer, the term of this patent is extended or adjusted under 35 U.S.C. 154(b) by 643 days.

This patent is subject to a terminal disclaimer.

(21) Appl. No.: 18/313,723

(22) Filed: May 8, 2023

(65) Prior Publication Data

US 2023/0278973 A1 Sep. 7, 2023

Related U.S. Application Data

(60) Continuation of application No. 17/222,611, filed on Apr. 5, 2021, now Pat. No. 11,661,405, which is a continuation of application No. 16/525,319, filed on Jul. 29, 2019, now Pat. No. 10,966,952, which is a division of application No. 15/579,705, filed as application No. PCT/IB2016/001181 on Jul. 19, 2016, now Pat. No. 10,413,519.

(60) Provisional application No. 62/195,486, filed on Jul. 22, 2015.

(51) Int. Cl.

| | |
|---|---|
| ***C07D 307/14*** | (2006.01) |
| ***A61K 31/341*** | (2006.01) |
| ***A61P 25/28*** | (2006.01) |
| ***B01D 9/00*** | (2006.01) |
| ***B01D 11/04*** | (2006.01) |

(52) U.S. Cl.

CPC ........... *C07D 307/14* (2013.01); *B01D 9/005* (2013.01); *B01D 11/0403* (2013.01); *B01D 11/0411* (2013.01); *A61K 31/341* (2013.01); *A61P 25/28* (2018.01)

(58) Field of Classification Search

None

See application file for complete search history.

(56) References Cited

U.S. PATENT DOCUMENTS

| | | | | |
|---|---|---|---|---|
| 10,413,519 | B2 * | 9/2019 | Daintree | B01D 11/0411 |
| 10,966,952 | B2 * | 4/2021 | Daintree | C07D 307/14 |
| 11,661,405 | B2 * | 5/2023 | Daintree | C07D 307/14 514/461 |

FOREIGN PATENT DOCUMENTS

| | | | |
|---|---|---|---|
| CN | 103539783 | A | 1/2014 |
| EP | 2873664 | A1 | 5/2015 |
| JP | 2007507497 | A | 3/2007 |
| JP | 2013523706 | A | 6/2013 |
| WO | 9501221 | A1 | 1/1995 |
| WO | 9600610 | A1 | 1/1996 |
| WO | 9730983 | A1 | 8/1997 |
| WO | 9836825 | A1 | 8/1998 |
| WO | 9944733 | A1 | 9/1999 |
| WO | 9959710 | A1 | 11/1999 |
| WO | 0103821 | A1 | 1/2001 |
| WO | 2005040113 | A1 | 5/2005 |
| WO | 2010097641 | A1 | 9/2010 |
| WO | 2011121308 | A1 | 10/2011 |
| WO | 2013008044 | A1 | 1/2013 |
| WO | 2014155138 | A1 | 10/2014 |

OTHER PUBLICATIONS

Office Action for Canadian Application No. 2,986,349, mailed on Jul. 25, 2024, 4 pages.
Office Action for Chinese Patent Application No. 20168033152, mailed on Aug. 5, 2024, 11 pages.
("Technology in Drug Separation", Editor in Chief Song, Hong et al; Huadong Science and Technology University Press, published Aug. 2011, Version 1, First Print, p. 285, portion in rectangle.).
("Strategy and Policy Appraisal on Chinese Pharmaceutical Sciences", Editor in Chief Wang, Guongji; China Pharmaceutical Sciences Press, published May 2002, Version 1, First Print, p. 248 (portion in rectangle)).
Communication Pursuant to Article 94(3) EPC for Application No. 16827324.1, mailed on Nov. 2, 2023, 6 pages.
Bouchard A., et al., "Ways of Manipulating the Polymorphism of Glycine During Supercritical Fluid Crystallisation," The Journal of Supercritical Fluids, Apr. 2008, vol. 44, No. 3, pp. 422-432.
Byrn S., et al., "Pharmaceutical Solids: A Strategic Approach to Regulatory Consideration," Pharmaceutical Rsearch, Aug. 1995, vol. 12(7), pp. 945-954.
Communication Pursuant to Article 94(3) EPC for European Patent Application No. 16827324.1, mailed Apr. 4, 2022, 9 Pages.
Extended European Search Report issued in European Application No. 16827324.1, mailed on Jan. 3, 2019, 9 pages.
Flack H.D., Chiral and Achiral Crystal Structures, Helvetica Chimica Acta, 2003, vol. 86, pp. 905-921.
Foscolos G. B., et al., "Synthesis and Pharmcological Study of Some new beta-(dialkylaminomethyl)-gamma-butyrolact ones and their Tetrahydrofuran Analogs," IL Farmaco, Feb. 1996, vol. 51(1), pp. 19-26.

(Continued)

*Primary Examiner* — Valerie Rodriguez-Garcia
(74) *Attorney, Agent, or Firm* — Polsinelli PC

(57) ABSTRACT

Polymorphic forms of tetrahydro-N,N-dimethyl-2,2-diphenyl-3-furanmethanamine hydrochloride (ANAVEX2-73) and a metabolite of tetrahydro-N,N-dimethyl-2,2-diphenyl-3-furanmethanamine hydrochloride (ANAVEX19-144) are disclosed and characterized. Compositions and method for treatment of Alzheimer's disease that includes the polymorphic forms and metabolite of tetrahydro-N,N-dimethyl-2,2-diphenyl-3-furanmethanamine hydrochloride (ANAVEX2-73).

9 Claims, 18 Drawing Sheets

(56) References Cited

OTHER PUBLICATIONS

Hirayama N., "Handbook for Preparing Crystals of Organic Compounds-Principle and Know-How," Maruzen Co., Ltd Jul. 25, 2008, 52 pages.
International Preliminary Report on Patentability for International PCT Patent Application No. PCT/IB2016/001181, mailed on Feb. 1, 2018, 9 pages.
International Search Report and Written Opinion in corresponding International application PCT/IB2016/001181, dated Jan. 1, 2017, 12 Pages.
Kagaku J., et al., "Experimental Chemistry Course 1, Basic Operation 1," Chemical Society of Japan, Fourth Edition, Apr. 5, 1996, Second Print, 6 pages.
Lahmy V., et al., "Blockade of Tau Hyperphosphorylation and a beta 1-42 Generation by the Aminotetrahydrofuran Derivative ANAVEX2-73, A Mixed Muscarinic and Gammal Receptor Agonist, in a Nontransgenic Mouse Model of Alzheimer's Disease," Neurophychopharmacology, Aug. 2013, vol. 38(9), pp. 1706-1723.
Nakai Y., et al., "Shinseizaigaku, New Pharmaceutics," NANZANDCO., Ltd, Apr. 25, 1984, first edition, 26 pages.
Office Action for Japanese Application No. 2017-564733 mailed on Aug. 2, 2021, 14 pages.
Office Action for Japanese Application No. 2017-564733 mailed on Aug. 6, 2020, 9 pages.
Office Action for Japanese Application No. 2017-564733 mailed on Jan. 20, 2023, 11 pages.
Office Action for Japanese Application No. 2021-018132 mailed on Aug. 26, 2022, 7 pages.
Rehman M., et al., Optimisation of Powders for Pulmonary Delivery Using Supercritical Fluid Technology, European Journal of Pharmaceutical Sciences, 2004, vol. 22, No. 1, pp. 1-17.
Second Office Action for Chinese Application No. 201680033152.9, mailed May 6, 2021, 14 Pages.
Shioji Y., "Manufacture Technology of Solid Tablet," CMC Publishing Co., Ltd, Jan. 27, 2003, Popular Edition, First Print, 10 pages.
Villard V., et al., "Anti-Amnesic and Neuroprotective Potentials of the Mixed Muscarinic Receptor/Sigma1 Ligand ANAVAEX2-73, a Novel Aminotetrahydrofuran Derivative," Journal of Psychopharmacology, Aug. 2011, vol. 25, No. 8, pp. 1101-1117.

* cited by examiner

B2201054 10mg in 0.7ml DMSO H NMR

| | | | | | | | |
|---|---|---|---|---|---|---|---|
| Acquisition Time (sec) | 1.9792 | Comment | B2201054 10mg in 0.7 DMSO H NMR | | | Date | 12 Jun 2015 15:17:36 |
| Date Stamp | 12 Jun 2015 15:17:36 | | | File Name | [illegible] | | |
| Frequency (MHz) | 400.13 | Nucleus | 1H | Number of Transients | 16 | Origin | DPX400 |
| Original Points Count | 16384 | Owner | Administrator | Points Count | 16384 | Pulse Sequence | zg30 |
| Receiver Gain | 362.00 | SW(cyclical)(Hz) | 8278.15 | Solvent | DMSO-d6 | Spectrum Offset (Hz) | 2470.9668 |
| Spectrum Type | STANDARD | Sweep Width (Hz) | 8277.64 | Temperature (degree C) | 24.160 | | |

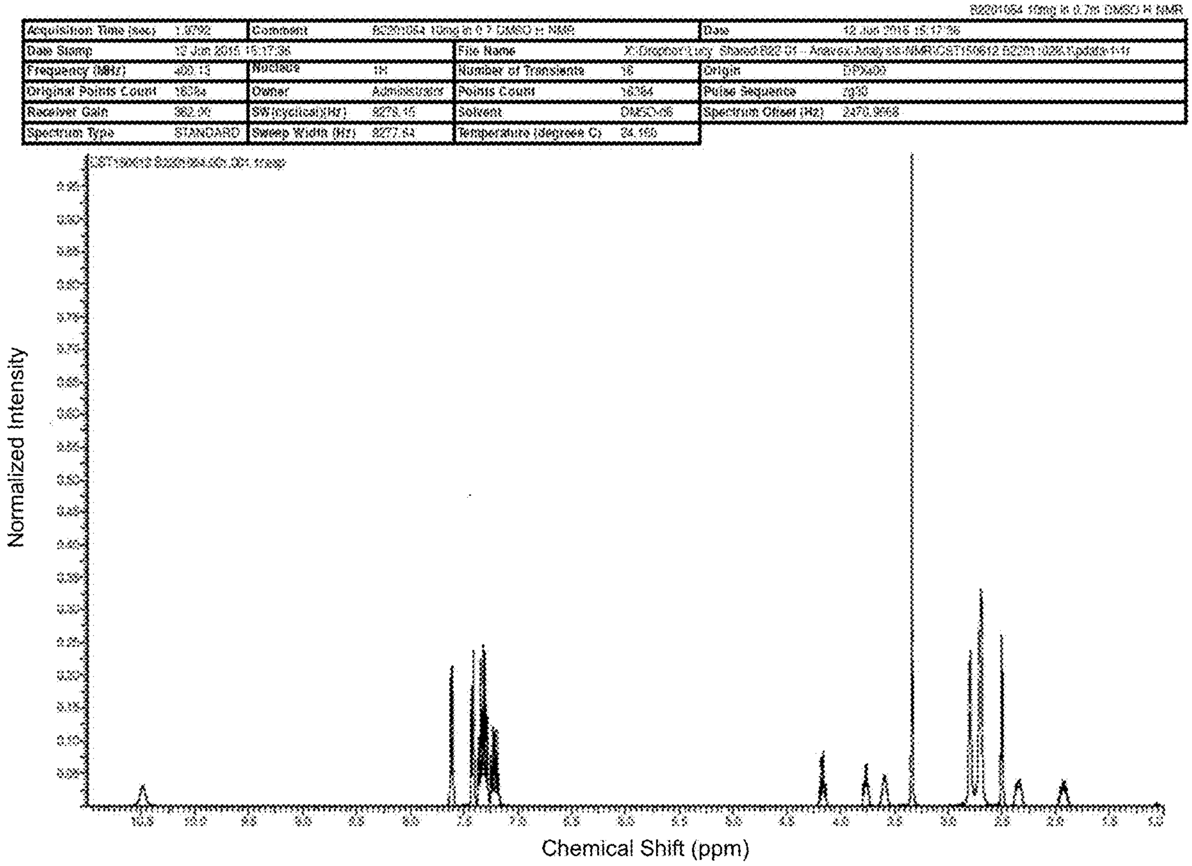

FIG. 10

CRYSTAL FORMS OF TETRAHYDRO-N,N-DIMETHYL-2,2-DIPHENYL-3-FURANMETHANAMINE, PROCESSES OF MAKING SUCH FORMS, AND THEIR PHARMACEUTICAL COMPOSITIONS

CROSS REFERENCED TO RELATED APPLICATIONS

This application is a divisional application of U.S. patent application Ser. No. 17/222,611 filed Apr. 5, 2021; which is a continuation of U.S. patent application Ser. No. 16/525,319 filed Jul. 29, 2019; which is a divisional of U.S. patent application Ser. No. 15/579,705 filed Dec. 5, 2017, which is the 35 U.S.C. 371 National Stage of International Application Number PCT/IB2016/001181, filed Jul. 19, 2016, which claims priority from U.S. Provisional Patent Application No. 62/195,486 filed Jul. 22, 2015, the entire contents of each of which are incorporated herein by reference.

FIELD

The present disclosure is directed to crystalline forms of tetrahydro-N,N-dimethyl-2,2-diphenyl-3-furanmethanamine hydrochloride, as well as compositions, processes of preparation, and uses thereof.

BACKGROUND

Because improved drug formulations showing, for example, better bioavailability or better stability are consistently sought, there is an ongoing need for more fully characterized, new, polymorphic and derivative forms of drug molecules. Characterization of tetrahydro-N,N-dimethyl-2,2-diphenyl-3-furanmethanamine hydrochloride, and crystalline polymorphs and a metabolite of tetrahydro-N,N-dimethyl-2,2-diphenyl-3-furanmethanamine hydrochloride are described herein toward this end.

SUMMARY OF THE PRESENT DISCLOSURE

The present disclosure comprises crystalline forms of tetrahydro-N,N-dimethyl-2,2-diphenyl-3-furanmethanamine hydrochloride characterized by the PXRD pattern shown in FIG. 1, FIG. 4, or FIG. 8. The crystalline forms are further characterized by the FTIR spectrum shown in FIG. 5 or FIG. 9. The crystalline forms are further characterized by the $^{1}$H-NMR spectrum shown in FIG. 6 or FIG. 10. The crystalline forms are further characterized by the particle shapes depicted in FIG. 2, FIG. 3, FIG. 7 or FIG. 11. The crystalline forms are further characterized by the particle sizes depicted in FIG. 2, FIG. 3, FIG. 7 or FIG. 11. The crystalline forms can have a plate-like habit. The crystalline forms can also have a needle-like habit. The crystalline forms can have a lath-like habit. Further included, is a method of making the crystalline forms using a supercritical fluid (SCF) technique. Further included is a dosage form comprising a therapeutically neuroprotective amount of the crystalline forms. Further included is a pharmaceutical composition for the treatment of Alzheimer's disease comprising a therapeutically effective amount of the crystalline forms. Further included is a method of treating Alzheimer's disease in a subject comprising administering to the subject a therapeutically effective amount of the crystalline forms.

The present disclosure also comprises crystalline Form I of tetrahydro-N,N-dimethyl-2,2-diphenyl-3-furanmethanamine hydrochloride characterized by the PXRD pattern shown in FIG. 1. The crystalline Form I according is also characterized by the particle shapes as depicted in FIG. 2. The crystalline Form I is also characterized by the particle shapes as depicted in FIG. 3. The crystalline Form I is also characterized by the particle sizes as depicted in FIG. 2. The crystalline Form I is also characterized by the particle sizes as depicted in FIG. 3. Crystalline Form I is also characterized by a plate-like habit. Further included is a method of making crystalline Form I using a supercritical fluid (SCF) technique. Further included is a dosage form comprising a therapeutically neuroprotective amount of crystalline Form I. Further included is a pharmaceutical composition for the treatment of Alzheimer's disease comprising a therapeutically effective amount of crystalline Form I. Further included is a method of treating Alzheimer's disease in a subject comprising administering to the subject a therapeutically effective amount of the crystalline Form I.

The present disclosure also comprises crystalline Form II of tetrahydro-N,N-dimethyl-2,2-diphenyl-3-furanmethanamine hydrochloride characterized by the PXRD pattern shown in FIG. 4. Crystalline Form II is also characterized by the FTIR spectrum shown in FIG. 5. Crystalline Form II is also characterized by the $^{1}$H-NMR spectrum shown in FIG. 6. Crystalline Form II is also characterized by particle shapes as depicted in FIG. 7. Crystalline Form II is also characterized by particle sizes as depicted in FIG. 7. Crystalline Form II can also have a plate-like habit. Further included is a method of making crystalline Form II using a supercritical fluid (SCF) technique. Further included is a dosage form comprising a therapeutically neuroprotective amount of crystalline Form II. Further included is a pharmaceutical composition for the treatment of Alzheimer's disease comprising a therapeutically effective amount of crystalline Form II. Further included is a method of treating Alzheimer's disease in a subject comprising administering to the subject a therapeutically effective amount of crystalline Form II.

The present disclosure also comprises crystalline Form III of tetrahydro-N,N-dimethyl-2,2-diphenyl-3-furanmethanamine hydrochloride characterized by the PXRD pattern shown in FIG. 8. Crystalline Form III is also characterized by the FTIR spectrum shown in FIG. 9. Crystalline Form III is also characterized by the $^{1}$H-NMR spectrum shown in FIG. 10. Crystalline Form III is also characterized by particle shapes as depicted in FIG. 11. Crystalline Form III is also characterized by particle sizes as depicted in FIG. 11. Crystalline Form III can also have a lath-like habit. Further included is a method of making crystalline Form III using a supercritical fluid (SCF) technique. Further included is a dosage form comprising a therapeutically neuroprotective amount of crystalline Form III. Further included is a pharmaceutical composition for the treatment of Alzheimer's disease comprising a therapeutically effective amount of crystalline Form III. Further included is a method of treating Alzheimer's disease in a subject comprising administering to the subject a therapeutically effective amount of crystalline Form III.

The present disclosure also comprises metabolite ANAVEX19-144 characterized by the PXRD pattern shown in FIG. 12. Metabolite ANAVEX19-144 is also characterized by the DSC-TGA data shown in FIG. 13. Metabolite ANAVEX19-144 is also characterized by the FTIR spectrum shown in FIG. 14. Metabolite ANAVEX19-144 can also be characterized by particle shapes as depicted in FIG. 15. Metabolite ANAVEX19-144 can also be characterized by particle sizes as depicted in FIG. 15. Metabolite ANAVEX19-144 can also have a needle-like habit. Further included is a method of making the metabolite ANAVEX19-144 using a supercritical fluid (SCF) technique. Further included is a dosage form comprising a therapeutically neuroprotective amount of the metabolite ANAVEX19-144. Further included is a pharmaceutical composition for the treatment of Alzheimer's disease comprising a therapeutically effective amount of the metabolite ANAVEX19-144. Further included is a method of treating Alzheimer's disease in a subject comprising administering to the subject a therapeutically effective amount of the metabolite ANAVEX19-144.

The present disclosure also comprises metabolite ANAVEX19-144 characterized by the PXRD pattern shown in FIG. 17. Metabolite ANAVEX19-144 is also characterized by the DSC-TGA data shown in FIG. 18. Metabolite ANAVEX19-144 can also be characterized by particle shapes as depicted in FIG. 16. Metabolite ANAVEX19-144 can also be characterized by particle sizes as depicted in FIG. 16. Further included is a method of making the metabolite ANAVEX19-144 using a supercritical fluid (SCF) technique. Further included is a dosage form comprising a therapeutically neuroprotective amount of metabolite ANAVEX19-144. Further included is a pharmaceutical composition for the treatment of Alzheimer's disease comprising a therapeutically effective amount of metabolite ANAVEX19-144. Further included is a method of treating Alzheimer's disease in a subject comprising administering to the subject a therapeutically effective amount of metabolite ANAVEX19-144.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 10 depicts a $^1$H-NMR spectrum characteristic of polymorph Form III of tetrahydro-N,N-dimethyl-2,2-diphenyl-3-furanmethanamine hydrochloride (ANAVEX2-73);

DETAILED DESCRIPTION

Figure 1:
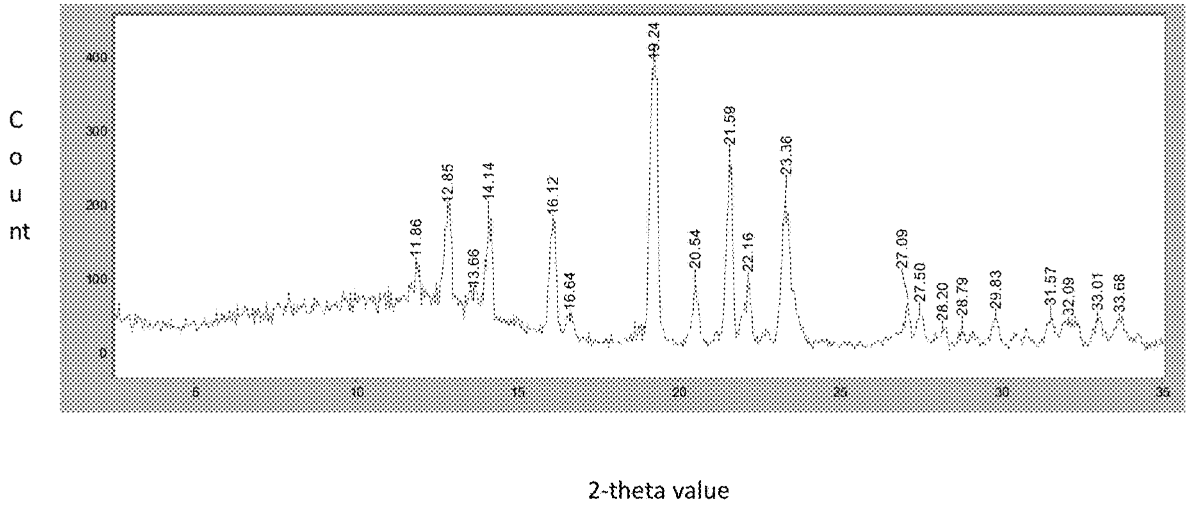
FIG. 1 depicts a powder X-ray diffraction (PXRD) pattern characteristic of polymorph Form I of tetrahydro-N,N-dimethyl-2,2-diphenyl-3-furanmethanamine hydrochloride (ANAVEX2-73)

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more embodiments are illustrated below, the disclosed method may be implemented using any number of techniques. The disclosure should in no way be limited to the illustrative implementations, drawings, and techniques illustrated herein, but may be modified within the scope of the appended claims along with their full scope of equivalents.

In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of this disclosure upon reading the following detailed description, and by referring to the accompanying drawings.

The present disclosure relates to tetrahydro-N,N-dimethyl-2,2-diphenyl-3-furanmethanamine hydrochloride, also referred to as ANAVEX2-73:

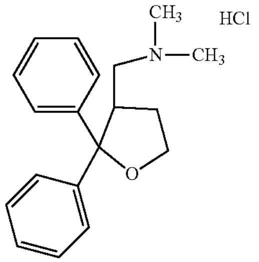 [SMILES: CN(C)CC1CCOC1(c1ccccc1)c1ccccc1 ; Cl]

It has been reported that ANAVEX2-73 shows neuroprotective potential against amyloid toxicity in mice. In particular, ANAVEX2-73 has been reported as attenuating oxidative stress, caspases induction, cellular loss and learning and memory deficits observed in mice one week after the i.c.v. injection of an oligomeric preparation of amyloid $ß_{25-35}$ peptide ($Aβ_{25-35}$). See J. Psychopharmacol. 25(8), 1101-1117 (2011). More recently, it has been reported that ANAVEX2-73 blocked the $Aβ_{25-35}$-induced P-Akt decrease and P-GSK-3β increase, indicating activation at the PI3K neuroprotective pathway. See Neuropsychopharmacology 38, 1706-1723

In the dose-range tested, ANAVEX2-73 attenuated the hyperphosphorylation of Tau on physiological epitopes (AT-8 antibody clone) and on pathological epitopes (AT-100 clone). ANAVEX2-73 also has been reported to decrease the $Aβ_{25-35}$-induced endogenous $Aβ_{1-42}$ seeding.

Reference is made to U.S. Patent Publication No. 2014/0296211 entitled "ANAVEX2-73 AND CERTAIN ANTICHOLINESTERASE INHIBITORS COMPOSITION AND METHOD FOR NEUROPROTECTION," to Vamvakides et al., filed Jul. 12, 2013; U.S. Ser. No. 62/065,833 entitled "A19-144, A2-73 AND CERTAIN ANTICHOLINESTERASE INHIBITOR COMPOSITIONS AND METHOD FOR ANTI-SEIZURE THERAPY," filed Oct. 20, 2014; U.S. Patent application entitled "ANAVEX2-73 FOR THE TREATMENT OF ALZHEIMER'S DISEASE" and filed on date even herewith; U.S. Patent application entitled "ENANTIOMERS OF A2-73, ANALOGUES, AND SIGMA AGONIST ACTIVITY" and filed on date even herewith. The teaching of these applications and publications and all references cited herein are incorporated by reference in their entirety.

The present disclosure, provides a crystalline polymorph (Form I) of tetrahydro-N,N-dimethyl-2,2-diphenyl-3-furanmethanamine hydrochloride, characterized by PXRD and other data provided herein.

The present disclosure provides another crystalline polymorph (Form II) of tetrahydro-N,N-dimethyl-2,2-diphenyl-3-furanmethanamine hydrochloride characterized by the PXRD and other data provided herein.

The present disclosure further provides another crystalline polymorph (Form III) of tetrahydro-N,N-dimethyl-2,2-diphenyl-3-furanmethanamine hydrochloride characterized by the PXRD and other data provided herein.

The present disclosure also provides a metabolite of tetrahydro-N,N-dimethyl-2,2-diphenyl-3-furanmethanamine hydrochloride, referred to as ANAVEX19-144, characterized by the PXRD and other data provided herein and having the structure:

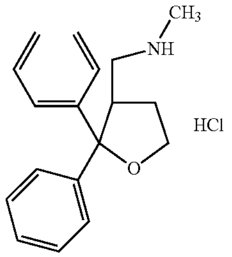 [SMILES: C=C/C=C(\C=C)C1(c2ccccc2)OCCC1CNC ; Cl]

The present disclosure further provides use of the polymorphs and metabolite material in the treatment of Alzheimer's disease.

Tetrahydro-N,N-dimethyl-2,2-diphenyl-3-furanmethanamine hydrochloride (ANAVEX2-73) was characterized by powder X-ray diffraction (PXRD), thermogravimetric analysis (TGA), differential scanning calorimetry (DSC), fourier transform infrared (FTIR) spectroscopy, proton nuclear magnetic resonance ($^1$H-NMR) and scanning electron microscopy (SEM), as detailed in FIGS. 1-15.

The present disclosure further provides processes of preparing the polymorphic forms of tetrahydro-N,N-dimethyl-2,2-diphenyl-3-furanmethanamine hydrochloride (ANAVEX2-73). In one embodiment, the polymorphic forms, disclosed herein, can be prepared by a supercritical fluid (SCF) anti-solvent process. In an embodiment, the anti-solvent is a supercritical fluid, although in some embodiments near-critical fluids may also be suitable. A "supercritical fluid" is a fluid at or above its critical pressure (Pc) and critical temperature (Tc) simultaneously. In practice, the pressure of the fluid is likely to be in the range between 1.01 and 7.0 of its critical pressure, and its temperature in the range between 1.01 and 4.0 of its critical temperature (in Kelvin). However, some fluids (e.g., helium and neon) have particularly low critical pressures and temperatures, 10 and may need to be used under operating conditions well in excess of those critical values, such as up to 200 times the relevant critical value. The term "near-critical fluid" encompasses both high pressure liquids, which are fluids at or above their critical pressure but below (although preferably close to) their critical temperature, and dense vapors, which are fluids at or above their critical 15 temperature but below (although preferably close to) their critical pressure. By way of example, a high pressure liquid might have a pressure between about 1.01 and 7 times its Pc, and a temperature between about 0.5 and 0.99 times its Tc. A dense vapor might, correspondingly, have a pressure between about 0.5 and 0.99 times its Pc, and a temperature between about 1.01 and 4 times its Tc.

Suitably, the anti-solvent and solution may be introduced into a precipitation chamber via respective passages with respective outlets, the outlets being arranged relative to one another such that anti-solvent introduced through a first passage and solution introduced through a second passage both enter the precipitation chamber at substantially the same point, which is substantially the point at which the anti-solvent and solution meet. To provide for good levels of mixing and dispersion, the anti-solvent and the solution may, for example, be co-fed into a precipitation chamber via a nozzle having co-axial passages which terminate adjacent to one another. Alternatively, one or more streams of the antisolvent may be arranged to impinge on a stream of the solution to provide good levels of mixing and dispersion. However, other mixing architectures are also possible.

Examples of suitable apparatus are known, inter alia, from WO-30 95/01221, WO-96/00610, WO-98/36825, WO-99/44733, WO-99/59710, WO-01/03821, and WO-03/008082, which are incorporated herein by reference.

According to the present disclosure, new crystalline forms of tetrahydro-N,N-dimethyl-2,2-diphenyl-3-furanmethanamine hydrochloride (ANAVEX2-73) were prepared by a supercritical fluid (SCF) process. The basic process involved preparing a solution of tetrahydro-N,N-dimethyl-2,2-diphenyl-3-furanmethanamine hydrochloride (ANAVEX2-73) in a suitable solvent, such as acetonitrile or ethanol, and introducing the solution to an SCF environment, typically supercritical $CO_2$, in a pressure vessel. The supercritical $CO_2$ acted as a powerful antisolvent allowing particles to be rapidly precipitated. Different polymorphic forms of tetrahydro-N,N-dimethyl-2,2-diphenyl-3-furanmethanamine hydrochloride (ANAVEX2-73) were produced by manipulating SCF process parameters, including the solvent used, flow rate, pressure, and temperature. Additionally, manipulation of SCF process parameters determined the size, morphology, and habit of crystalline particles produced by the SCF process.

Figure 2:
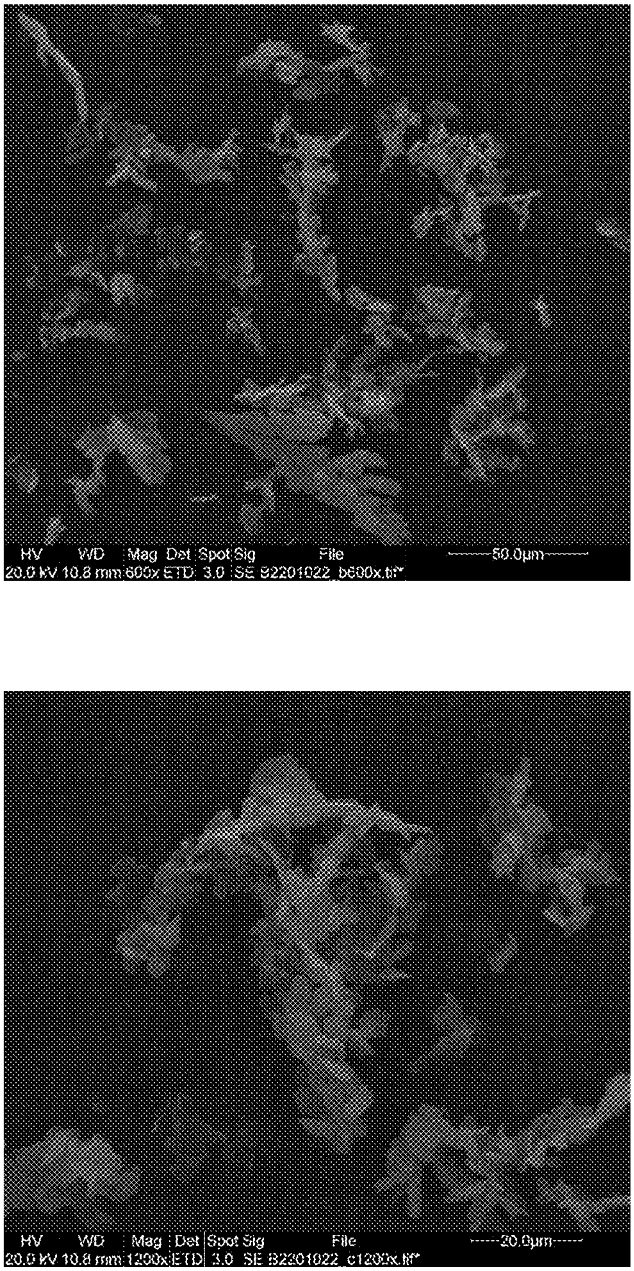
FIG. 2 depicts scanning electron microscope (SEM) micrographs demonstrating the size and morphology of particles of polymorph Form 1 of tetrahydro-N,N-dimethyl-2,2-diphenyl-3-furanmethanamine hydrochloride (ANAVEX2-73) produced using acetonitrile as the solvent in the supercritical fluid process.
Figure 3:
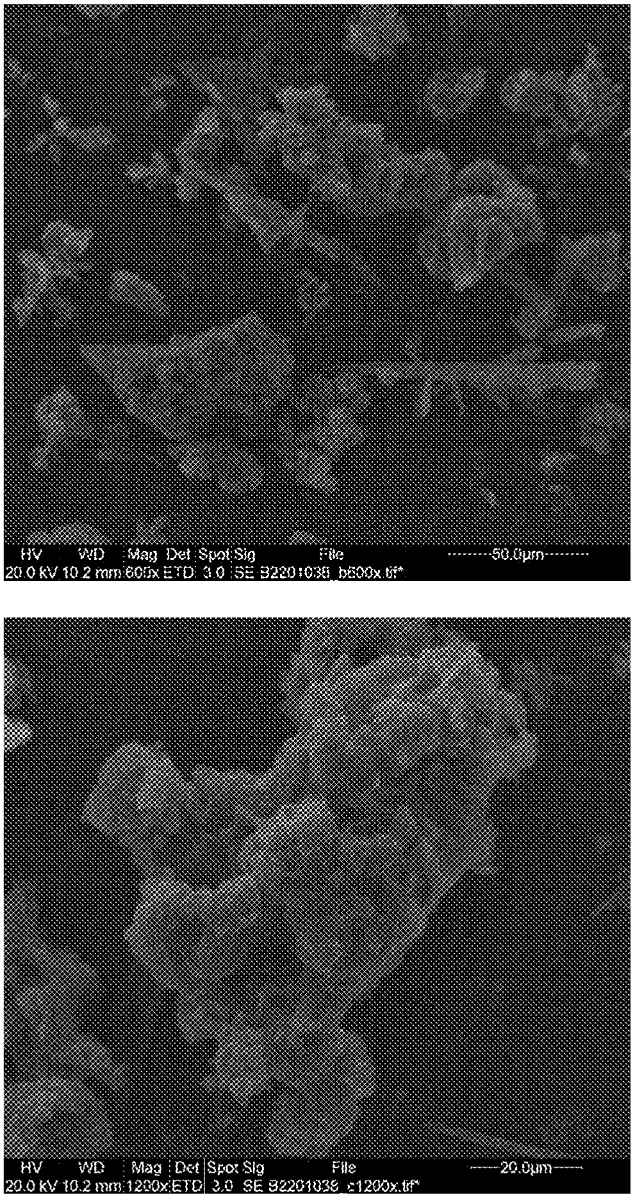
FIG. 3 depicts SEM micrographs demonstrating the size and morphology of particles of polymorph Form 1 of tetrahydro-N,N-dimethyl-2,2-diphenyl-3-furanmethanamine hydrochloride (ANAVEX2-73) produced using ethanol as the solvent in the supercritical fluid process.

The SCF process parameters used to produce the three polymorphic forms of tetrahydro-N,N-dimethyl-2,2-diphenyl-3-furanmethanamine hydrochloride (ANAVEX2-73), Forms I-III, are provided in Tables 1-3. As shown in Table 1, crystalline Form I was produced by placing the ANAVEX2-73 starting material in a solvent of acetonitrile or ethanol and processed by the supercritical fluid technique. The resulting particle shape differed depending upon the solvent. The particle shape for the crystalline Form I produced using acetonitrile solvent was plate-like. As used herein, the term “plate-like” refers to a flat particle of similar length and width. The particle shape for the crystalline Form I produced using ethanol solvent was a conglomerate. As used herein, the term “conglomerate” refers to a mixture of two or more types of particle shapes. The resulting material was characterized by PXRD and SEM. The PXRD for crystalline Form I of ANAVEX2-73 is shown in FIG. 1. SEM micrographs showing the particle size and morphology of crystalline Form I are shown in FIGS. 2-3. FIG. 2 shows the particle size and morphology of crystalline Form I produced using acetonitrile solvent (plate-like morphology). FIG. 3 shows the particle size and morphology of crystalline Form I produced using ethanol as the solvent (conglomerate morphology).

Figure 4:
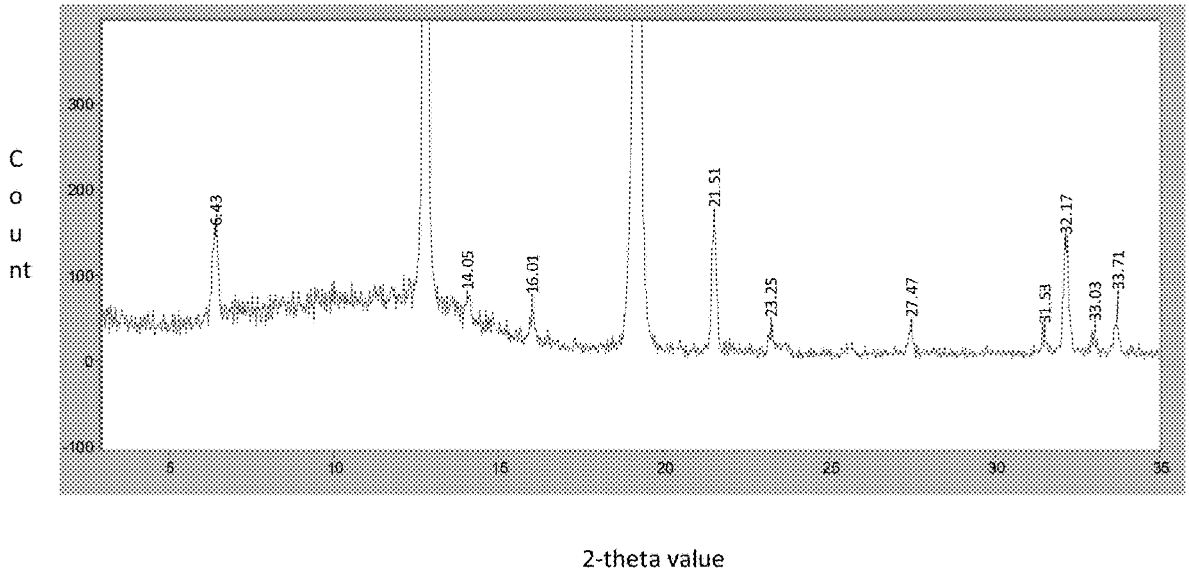
FIG. 4 depicts a PXRD pattern characteristic of polymorph Form II of tetrahydro-N,N-dimethyl-2,2-diphenyl-3-furanmethanamine hydrochloride (ANAVEX2-73)
Figure 5:
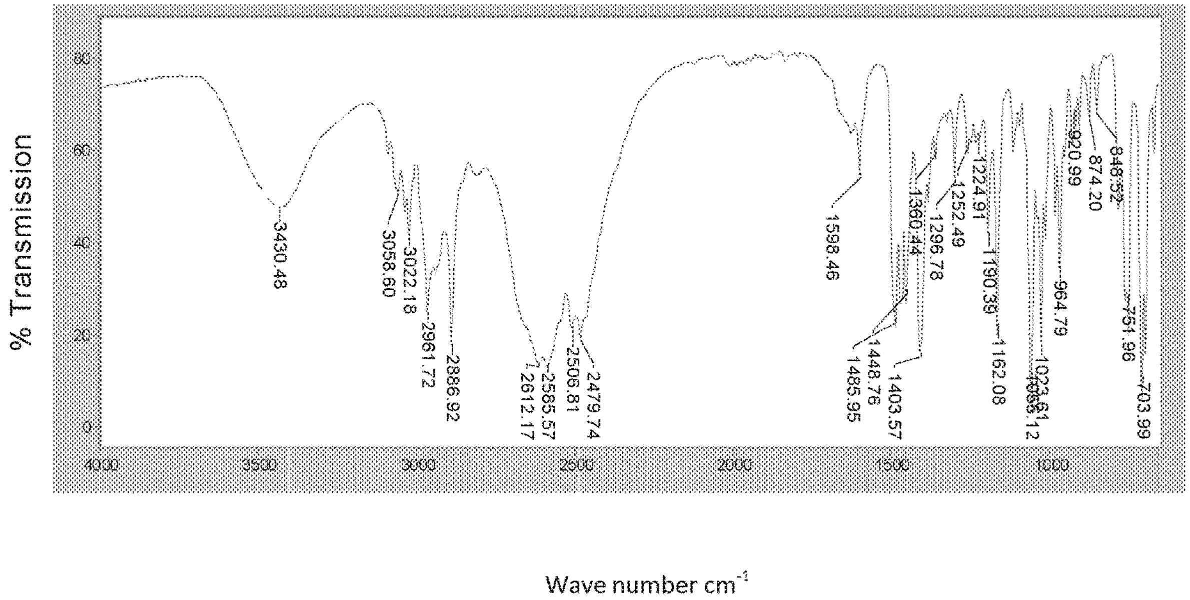
FIG. 5 depicts a fourier transform infrared (FTIR) spectrum characteristic of polymorph Form II of tetrahydro-N,N-dimethyl-2,2-diphenyl-3-furanmethanamine hydrochloride (ANAVEX2-73)
Figure 6:
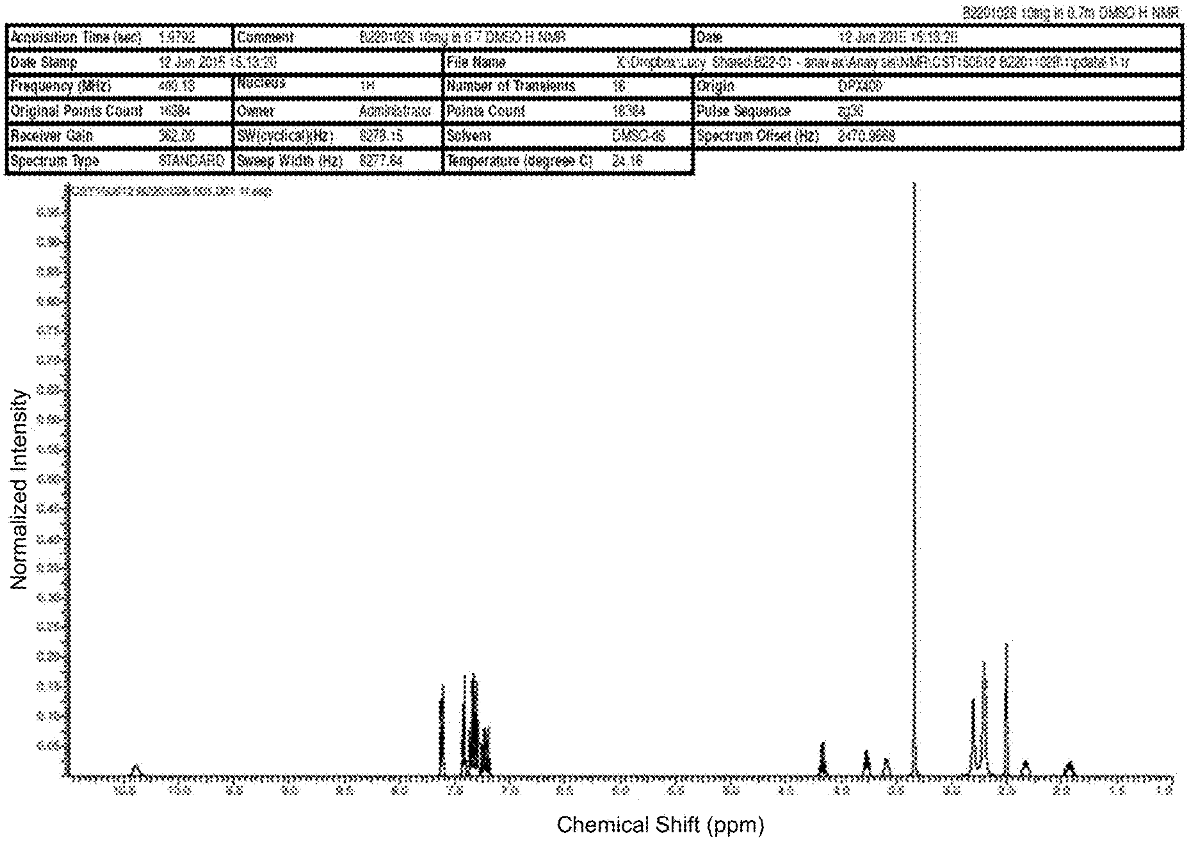
FIG. 6 depicts a proton nuclear magnetic resonance ($^1$H-NMR) spectrum characteristic of polymorph Form II of tetrahydro-N,N-dimethyl-2,2-diphenyl-3-furanmethanamine hydrochloride (ANAVEX2-73)
Figure 7:
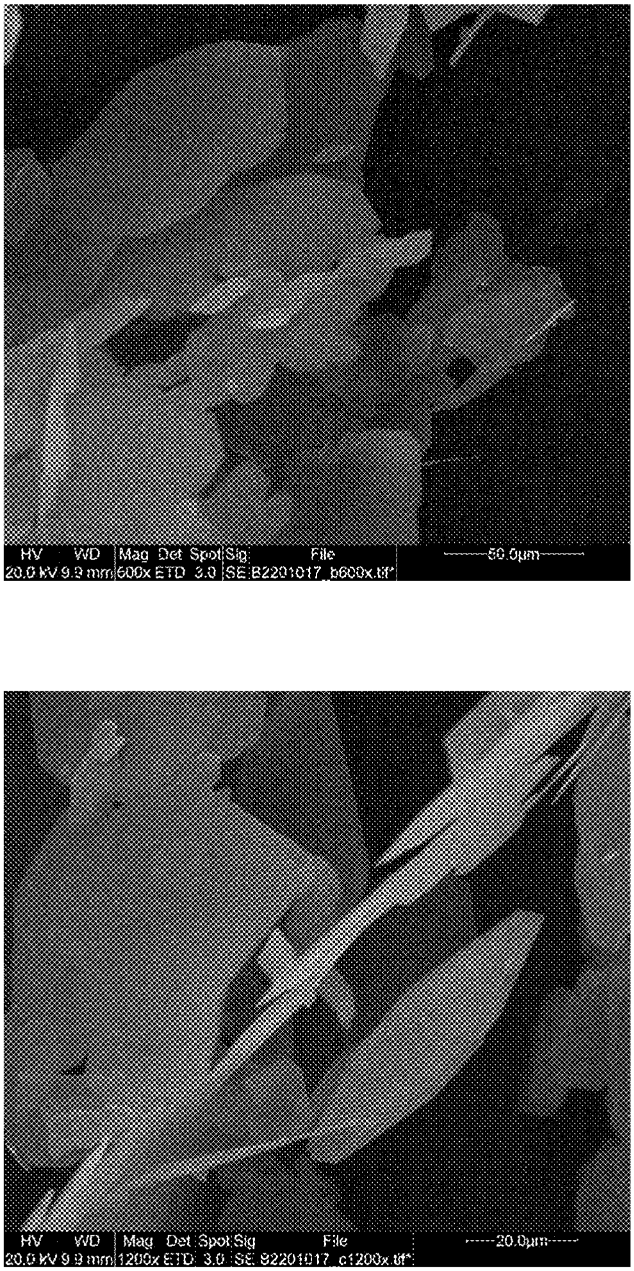
FIG. 7 depicts SEM micrographs demonstrating the size and morphology of particles of polymorph Form II of tetrahydro-N,N-dimethyl-2,2-diphenyl-3-furanmethanamine hydrochloride (ANAVEX2-73)

As shown in Table 2, crystalline Form II was produced by placing the ANAVEX2-73 starting material in a solvent of acetonitrile, 1:9 v/v trifluoroethanol+ethanol, 1:1 v/v acetone+ethanol, or 3-methyl-1-butanol, and processed by the supercritical fluid technique. In all cases, crystalline Form II was characterized by a plate-like habit. The resulting material was characterized by PXRD and SEM. The PXRD for crystalline Form II of ANAVEX2-73 is shown in FIG. 4. Crystalline Form II is further characterized by the FTIR spectrum shown in FIG. 5 and the $^1$H-NMR shown in FIG. 6. SEM micrographs showing the particle size and morphology of crystalline Form II are shown in FIG. 7.

Figure 8:
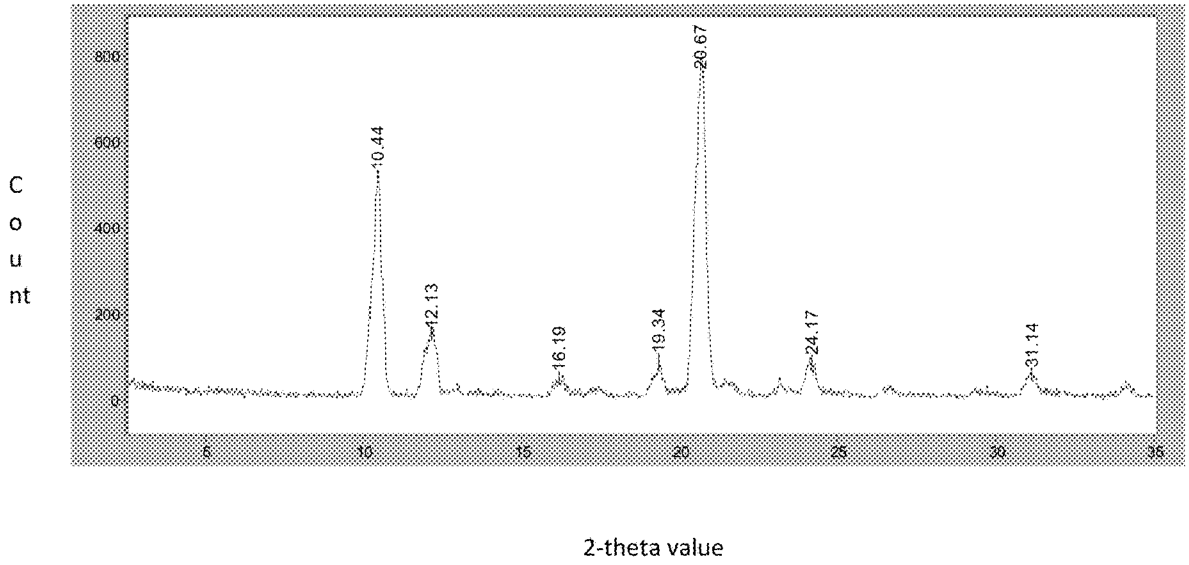
FIG. 8 depicts a PXRD pattern characteristic of polymorph Form III of tetrahydro-N,N-dimethyl-2,2-diphenyl-3-furanmethanamine hydrochloride (ANAVEX2-73)
Figure 9:
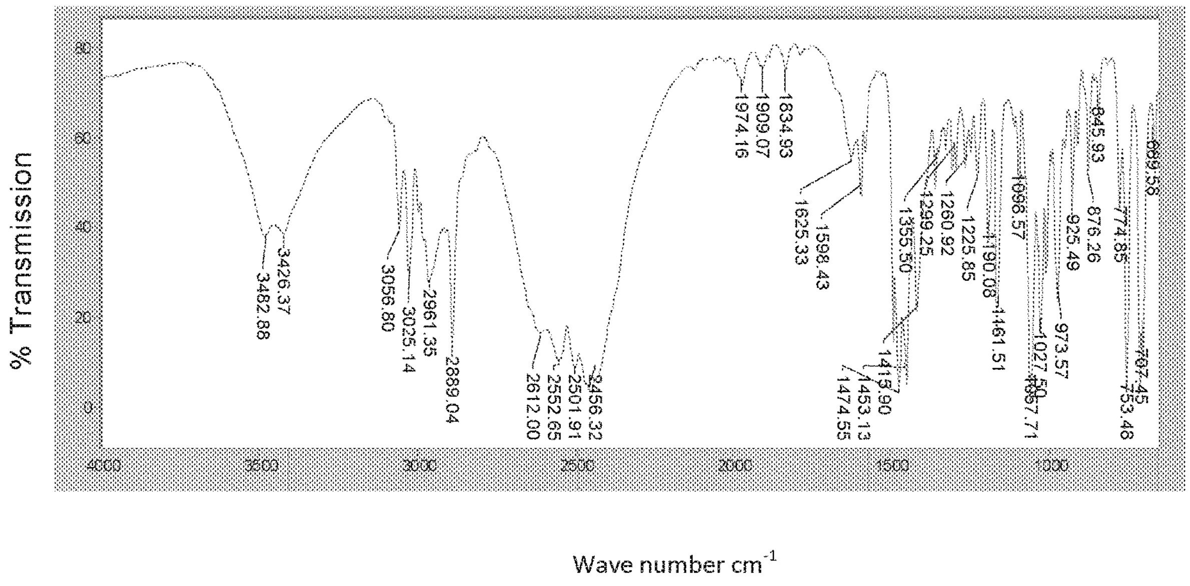
FIG. 9 depicts an FTIR spectrum characteristic of polymorph Form III of tetrahydro-N,N-dimethyl-2,2-diphenyl-3-furanmethanamine hydrochloride (ANAVEX2-73)
Figure 11:
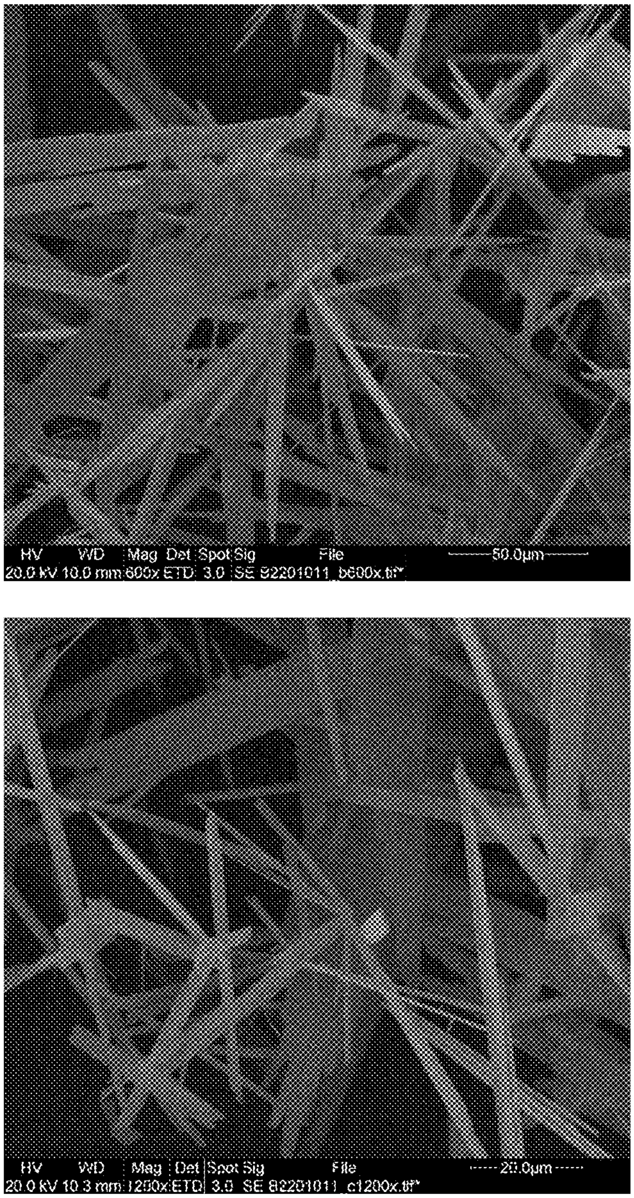
FIG. 11 depicts SEM micrographs demonstrating the size and morphology of particles of polymorph Form III of tetrahydro-N,N-dimethyl-2,2-diphenyl-3-furanmethanamine hydrochloride (ANAVEX2-73)
Figure 12:
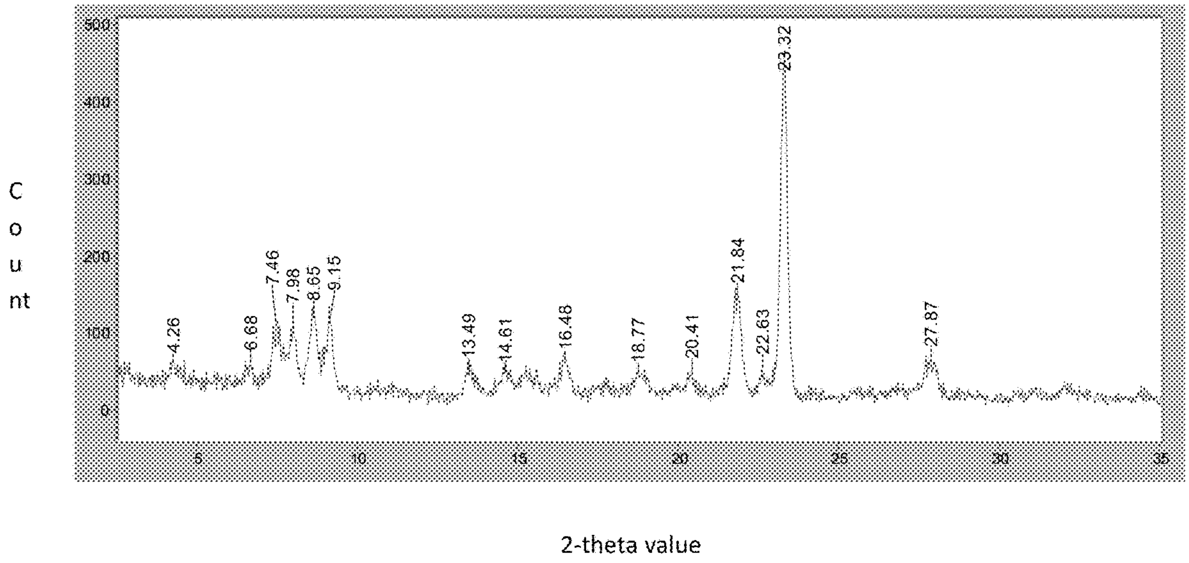
FIG. 12 depicts a PXRD pattern characteristic of metabolite ANAVEX19-144 produced using ethanol as the solvent in the supercritical fluid process.
Figure 13:
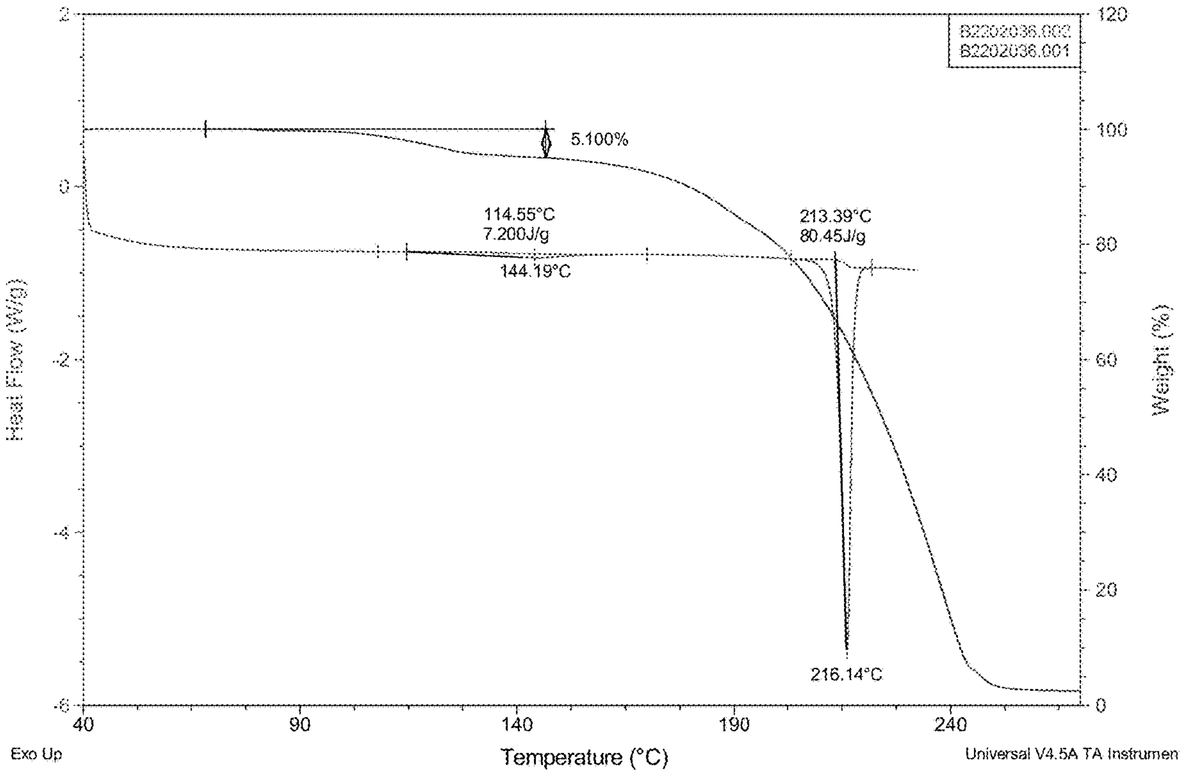
FIG. 13 depicts DSC-TGA data characteristic of metabolite ANAVEX19-144 produced using ethanol as the solvent in the supercritical fluid process.
Figure 14:
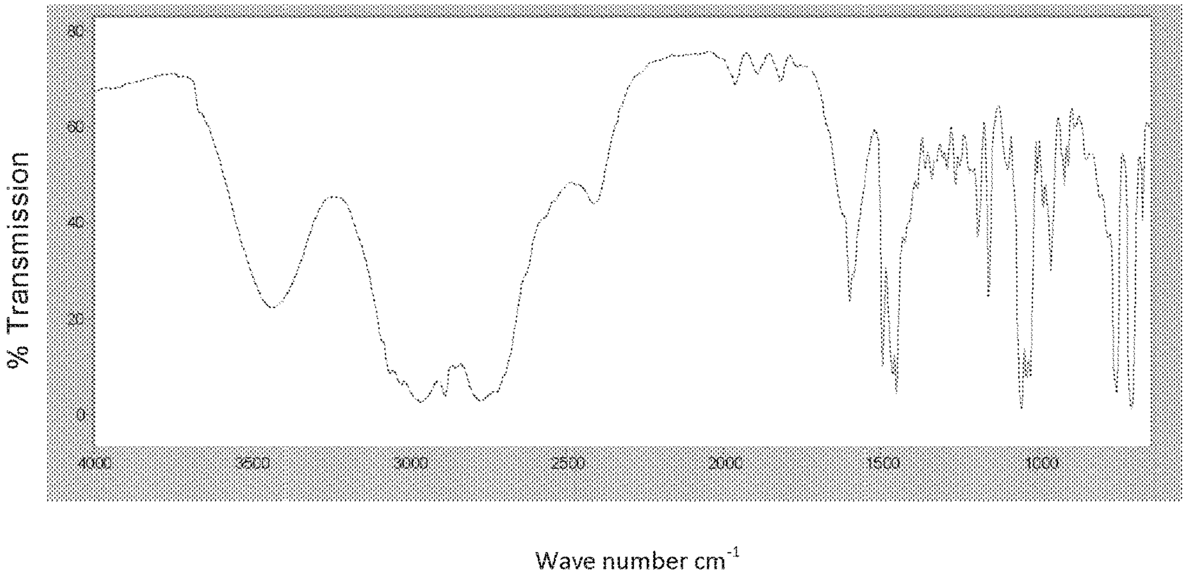
FIG. 14 depicts a FTIR spectrum characteristic of metabolite ANAVEX19-144 produced using ethanol as the solvent in the supercritical fluid process.

As shown in Table 3, crystalline Form III was produced by placing the ANAVEX2-73 starting material in a solvent of ethanol or 1:9 v/v trifluoroethanol+ethanol and processed by the supercritical fluid technique. In all cases, crystalline Form III was characterized by a lath-like habit. As used herein, “lath-like” refers to a long, thin blade-like particle. The resulting material was characterized by PXRD and SEM. The PXRD for crystalline Form III of ANAVEX2-73 is shown in FIG. 8. Crystalline Form III is further characterized by the FTIR spectrum shown in FIG. 9 and the $^1$H-NMR shown in FIG. 10. SEM micrographs showing the particle size and morphology of crystalline Form III are shown in FIG. 11.

TABLE 2

Crystalline Form II Samples

| SCF sample No | Solvent | Solution Conc (mg/ml) | P (bar) | T ° C. | density (g/cm$^3$) | TS flow (g/min) | CO$^2$ flow (g/min) | mole fraction $CO_2$ | mole fraction sol | Mass Ratio Flows | Particle shape | Surface characteristics |
|---|---|---|---|---|---|---|---|---|---|---|---|---|
| B2201017 | acetonitrile | 27.3 | 85 | 40 | 0.354 | 0.9432 | 20 | 0.955 | 0.045 | 21.20 | plate | smooth |
| B2201018 | acetonitrile | 27.3 | 200 | 40 | 0.84 | 0.9432 | 20 | 0.955 | 0.045 | 21.20 | plate | smooth |
| B2201020 | acetonitrile | 27.3 | 200 | 80 | 0.594 | 0.9432 | 20 | 0.955 | 0.045 | 21.20 | plate | smooth |
| B2201028 | acetonitrile | 27.3 | 85 | 40 | 0.354 | 1.5720 | 20 | 0.927 | 0.073 | 12.72 | plate | smooth |
| B2201039 | acetonitrile | 13 | 105 | 60 | 0.322 | 1.5720 | 20 | 0.927 | 0.073 | 12.72 | plate | smooth |
| B2201052 | 1:9 v/v trifluoroethanol + ethanol | 50 | 85 | 40 | 0.354 | 1.0120 | 20 | 0.952 | 0.048 | 19.76 | plate | smooth |
| B2201053 | 1:9 v/v trifluoroethanol + ethanol | 50 | 85 | 40 | 0.354 | 1.0120 | 20 | 0.952 | 0.048 | 19.76 | plate | smooth |
| B2201055 | 1:9 v/v trifluoroethanol + ethanol | 50 | 200 | 40 | 0.84 | 0.1687 | 20 | 0.992 | 0.008 | 118.57 | plate | smooth |
| B2201057 | 1:9 v/v trifluoroethanol + ethanol | 20 | 200 | 40 | 0.84 | 1.6867 | 20 | 0.922 | 0.078 | 11.86 | plate | smooth |
| B2201067 | 1:1 v/v acetone + ethanol | 50 | 85 | 40 | 0.354 | 1.5800 | 20 | 0.927 | 0.073 | 12.66 | plate | smooth |
| B2201072 | 1:1 v/v acetone + ethanol | 50 | 200 | 40 | 0.84 | 1.5800 | 20 | 0.927 | 0.073 | 12.66 | plate | smooth |
| B2201076 | 3-methyl-1-butanol | 10 | 85 | 40 | 0.354 | 0.9725 | 20 | 0.954 | 0.046 | 20.57 | plate | smooth |
| B2201077 | 3-methyl-1-butanol | 10 | 85 | 40 | 0.354 | 1.6208 | 20 | 0.925 | 0.075 | 12.34 | plate | smooth |

TABLE 1

| Crystalline Form I Samples | | | | | | | | | | | | |
|---|---|---|---|---|---|---|---|---|---|---|---|---|
| SCF sample No | Solvent | Solution Conc (mg/ml) | P (bar) | T ° C. | density (g/cm$^3$) | TS flow (g/min) | $CO_2$ flow (g/min) | mole fraction $CO_2$ | mole fraction sol | Mass Ratio Flows | Particle shape | Surface characteristics |
| B2202022 | acetonitrile | 27.3 | 105 | 60 | 0.322 | 0.4716 | 20 | 0.977 | 0.023 | 42.41 | plate | smooth |
| B2202038 | ethanol | 40 | 125 | 80 | 0.318 | 0.0789 | 20 | 0.996 | 0.004 | 253.49 | conglomerate | N/A |

TABLE 3

| Crystalline Form III Samples | | | | | | | | | | | | |
|---|---|---|---|---|---|---|---|---|---|---|---|---|
| SCF sample No | Solvent | Solution Conc (mg/ml) | P (bar) | T ° C. | density (g/cm$^3$) | TS flow (g/min) | $CO_2$ flow (g/min) | mole fraction $CO_2$ | mole fraction sol | Mass Ratio Flows | Particle shape | Surface characteristics |
| B2201011 | ethanol | 40 | 85 | 40 | 0.354 | 0.4734 | 20 | 0.977 | 0.023 | 42.25 | lath | smooth |
| B2201036 | ethanol | 40 | 200 | 40 | 0.84 | 1.5780 | 20 | 0.927 | 0.073 | 12.67 | lath | smooth |
| B2201054 | 1:9 v/v trifluoroethanol + ethanol | 50 | 85 | 40 | 0.354 | 0.1687 | 20 | 0.992 | 0.008 | 118.57 | lath | cracked |

Figure 15:
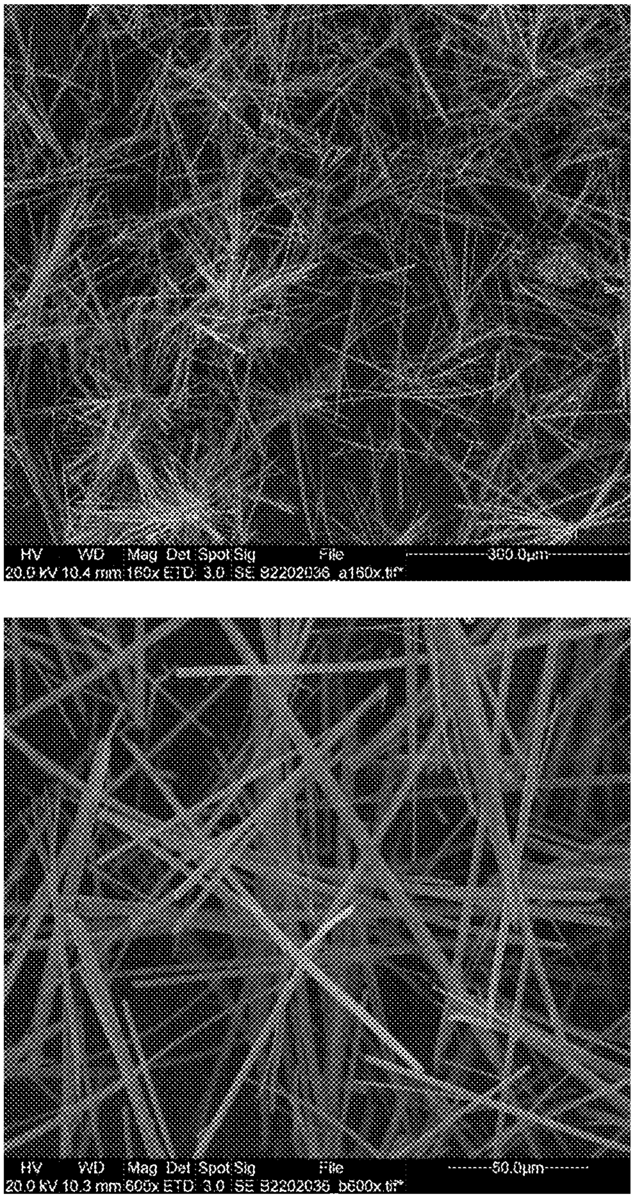
FIG. 15 depicts SEM micrographs demonstrating the size and morphology of particles of metabolite ANAVEX19-144 produced using ethanol as the solvent in the supercritical fluid process.
Figure 16:
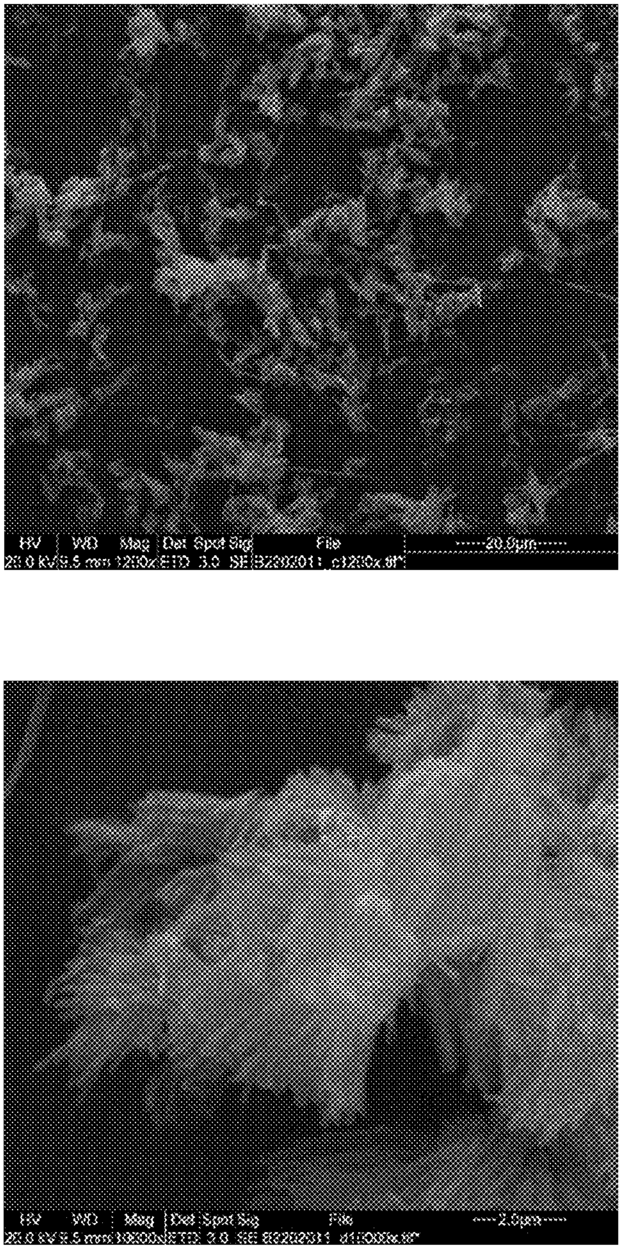
FIG. 16 depicts SEM micrographs demonstrating the size and morphology of particles of metabolite ANAVEX19-144 produced using dichloromethane as the solvent in the supercritical fluid process.
Figure 17:
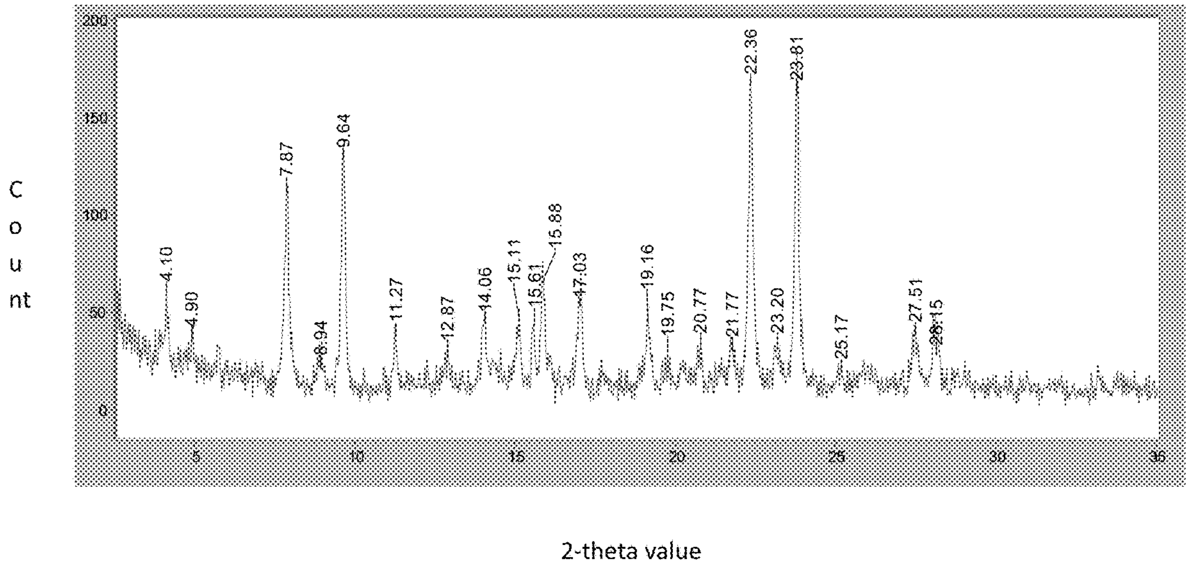
FIG. 17 depicts a PXRD pattern characteristic of metabolite ANAVEX19-144 produced using dichloromethane as the solvent in the supercritical fluid process.
Figure 18:
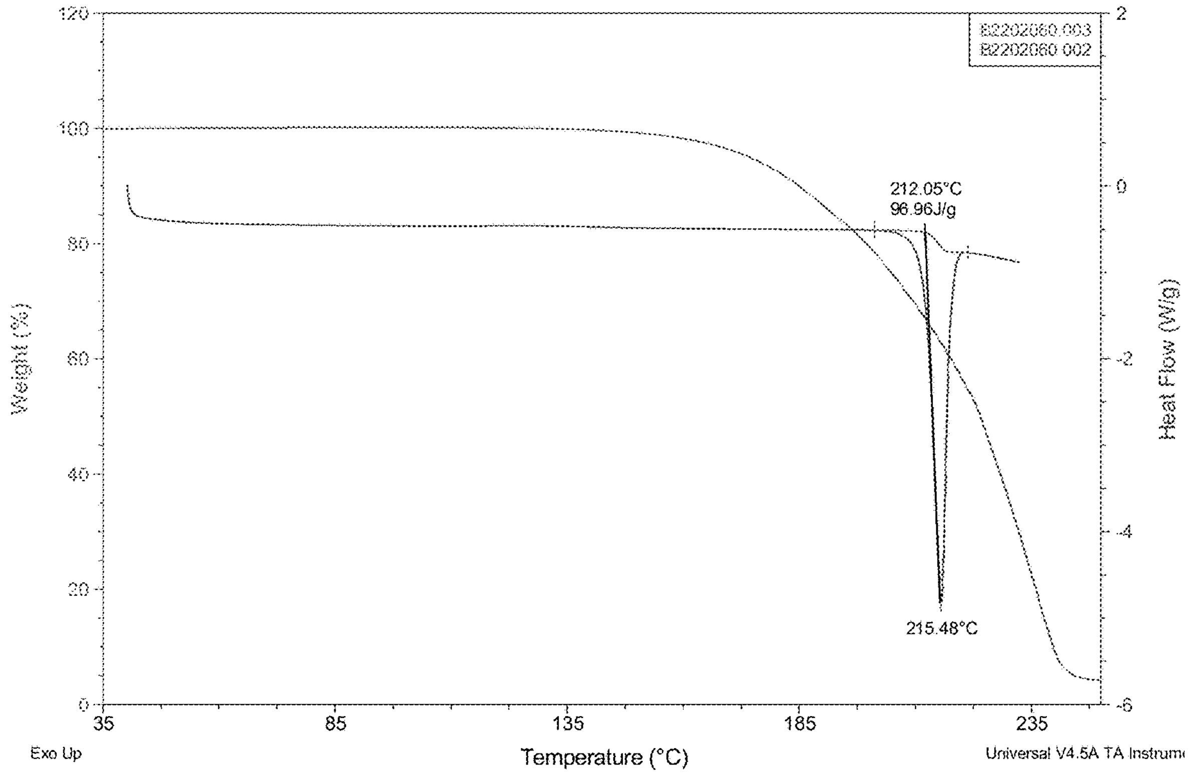
FIG. 18 depicts DSC-TGA data characteristic of metabolite ANAVEX19-144 produced using dichloromethane as the solvent in the supercritical fluid process.

The present disclosure also provides a metabolite of tetrahydro-N,N-dimethyl-2,2-diphenyl-3-furanmethanamine hydrochloride, ANAVEX19-144. ANAVEX19-144 has documented anti-amnesic and neuroprotective potentials similar to ANAVEX2-73. See for example J. of Psychopharmacol. 25(8), 1101-1117 (2011). Crystalline forms of ANAVEX19-144 were produced by placing the ANAVEX19-144 starting material in a solvent of ethanol or dichloromethane and processed by the supercritical fluid technique. The crystalline form of ANAVEX19-144 produced by the supercritical fluid technique under process parameters of 40 mg/mL ethanol solution, 200 bars of pressure, temperature of 80° C., supercritical $CO_2$ solution with a flow rate of 20 g/min and a TS flow of 0.4 mL/min, was characterized by PXRD, FTIR, DSC, and SEM, as shown in FIGS. 12-15. As shown in FIG. 15, the crystalline form of ANAVEX19-144 was characterized by needle-like crystals. In contrast, the crystalline form of ANAVEX19-144 produced by similar process parameters using the solvent dichloromethane exhibited a mixed habit of needle-like and lath-type particles, as shown in FIG. 16. The crystalline form of ANAVEX19-144 produced using the dichloromethane supercritical fluid technique produced a powder with better flow characteristics and improved flow properties for downstream processing. The crystalline form of ANAVEX19-144 was further characterized by PXRD and DSC, as shown in FIGS. 17-18. The two crystalline forms of ANAVEX19-144, produced according to the supercritical fluid technique in ethanol or dichloromethane were stored at 40° C. at 75% relative humidity in uncapped vessels for 1 week and then characterized by PXRD to determine stability of the two forms. After one week, the PXRDs for the two forms did not show any differences and therefore indicated that the two forms were stable under the conditions tested.

What is claimed is:

1. A composition comprising a crystal form of tetrahydro-N,N-dimethyl-2,2-diphenyl-3-furanmethanamine hydrochloride (ANAVEX2-73) made by crystallizing ANAVEX2-73 in a supercritical fluid (SCF) environment, wherein the supercritical fluid comprises supercritical carbon dioxide; and wherein the crystal form is characterized by an X-ray diffraction pattern of FIG. 1, FIG. 4, or FIG. 8.

2. The composition comprising a crystal form of claim 1, wherein the crystallizing comprises:

a. making a solution of ANAVEX2-73 in a solvent;

b. introducing the solution to the SCF;

c. allowing crystallization of ANAVEX2-73 in the SCF environment to form crystals;

and d. isolating the crystals, thus obtaining the crystal form.

3. The composition comprising a crystal form of claim 2, wherein the solvent comprises ethanol, acetonitrile, isopropyl alcohol, trifluoroethanol, acetone, 2-ethoxyethanol, 1-propanol, dichloromethane, dimethyl sulfoxide, N,N'-dimethylacetamide, dimethylformamide, trifluoroethanol, 1:9 v/v trifluoroethanol+ethanol, 1:1 v/v acetone+ethanol, 3-methyl-1-butanol, N-methyl-2-pyrrolidone, tert-butanol, or a combination thereof.

4. The composition comprising a crystal form of claim 2, wherein the SCF environment comprises pressure from about 85 bar to about 200 bar, and temperature ranging from about 40° C. to about 80° C.

5. The composition comprising a crystal form of claim 1, wherein the crystal form characterized by the X-ray diffraction pattern of FIG. 4 is further characterized by the FTIR spectrum of FIG. 5; and wherein the crystal form characterized by the X-ray diffraction pattern of FIG. 8 is further characterized by the FTIR spectrum of FIG. 9.

6. The composition comprising a crystal form of claim 1, wherein the crystal form characterized by the X-ray diffraction pattern of FIG. 1 is further characterized by the particle shapes of FIG. 2 or FIG. 3; wherein the crystal form characterized by the X-ray diffraction pattern of FIG. 4 is further characterized by the particle shapes of FIG. 7; and wherein the crystal form of FIG. 8 is further characterized by the particle shapes of FIG. 11.

7. The composition comprising a crystal form of claim 1, further characterized by a plate-like, conglomerate-like, or lath-like habit.

8. The composition comprising a crystal form of claim 1, wherein the crystal form is i. Crystal Form I, which is characterized by the X-ray diffraction pattern of FIG. 1, and particle size and morphology as shown in FIG. 2 or FIG. 3;

ii. Crystal Form II; which is characterized by the X-ray diffraction pattern of FIG. 4, and the FTIR spectrum of FIG. 5; or iii. Crystal Form III, which is characterized by the X-ray diffraction pattern of FIG. 8, and the FTIR spectrum of FIG. 9.

9. The composition comprising a crystal form of claim 8, wherein i. the Crystal Form II is further characterized by the particle size and morphology as shown in FIG. 7; or ii. the Crystal Form III is further characterized by the particle size and morphology as shown in FIG. 11.

* * * * *